United States Patent
Moore, Jr. et al.

(10) Patent No.: US 8,480,625 B2
(45) Date of Patent: Jul. 9, 2013

(54) GROOVED ASPIRATION PUMP ROLLER-HEAD ASSEMBLY

(75) Inventors: Thomas G. Moore, Jr., Kirkwood, MO (US); Ronald D. Spoor, Penn Yan, NY (US)

(73) Assignee: Bausch & Lamb Incorporated, Rochester, NY (US)

( * ) Notice: Subject to any disclaimer, the term of this patent is extended or adjusted under 35 U.S.C. 154(b) by 1597 days.

(21) Appl. No.: 11/585,045

(22) Filed: Oct. 23, 2006

(65) Prior Publication Data

US 2008/0097320 A1    Apr. 24, 2008

(51) Int. Cl.
A61M 1/00 (2006.01)
A61M 31/00 (2006.01)
A61M 37/00 (2006.01)
F04B 43/08 (2006.01)
F04B 43/12 (2006.01)
F04B 45/06 (2006.01)

(52) U.S. Cl.
USPC ........... 604/153; 604/500; 604/133; 604/151; 417/477.3

(58) Field of Classification Search
USPC .............. 604/30, 34, 35, 131–133, 151, 153, 604/500, 521; 417/477.1, 477.3
See application file for complete search history.

(56) References Cited

U.S. PATENT DOCUMENTS

| 4,861,242 A | 8/1989 | Finterwald ................. 417/477 |
| 5,387,088 A * | 2/1995 | Knapp et al. ................. 417/53 |
| 5,588,815 A | 12/1996 | Zaleski, II ................. 417/477.2 |
| 2005/0069419 A1 | 3/2005 | Cull et al. ................. 417/53 |

OTHER PUBLICATIONS

International Search Report (PCTISA/210) and Written Opinion (PCT/ISA/237) mailed on Jan. 29, 2008.

* cited by examiner

*Primary Examiner* — Bhisma Mehta
(74) *Attorney, Agent, or Firm* — Jeffrey B. Powers

(57) ABSTRACT

An ophthalmic aspiration pump roller-head assembly 10, includes a plurality of rollers 12, a base 16 attached to a first end of the rollers 12, and a face-plate 18 attached to a second end of the rollers 12. The face-plate 18 has at least one groove formed in the face-plate 18 for drawing a tube onto the rollers 12.

3 Claims, 4 Drawing Sheets

GROOVED ASPIRATION PUMP ROLLER-HEAD ASSEMBLY

BACKGROUND OF THE INVENTION

1. Field of the Invention

The present invention is directed towards a grooved aspiration pump roller-head assembly. More particularly, the present invention is directed towards a self-engaging peristaltic pump head having a thread for pulling a loop of tubing onto the roller-head assembly.

2. Description of Related Art

It is well known for a peristaltic pump to use a pump cartridge having a loop of tubing which is placed over a roller-head assembly. The tubing is then either stretched, such that the tubing is pinched off between the rollers of the roller-head assembly or is pressed between the rollers and a backing plate. When the roller-head assembly is rotated, fluid is peristaltically pumped through the loop of tubing from a surgical site.

To ensure proper operation of the peristaltic pump, it is necessary that the loop of tubing is properly mounted on the roller-head assembly. There have been many known schemes to ensure the tubing is properly loaded onto the roller-head assembly. These include U.S. Pat. No. 4,861,242 to Finsterwald and U.S. Pat. No. 5,588,815 to Zaleski, II. These two patents both teach the use of a notch which extends beyond a forward face of a roller-head assembly and acts to engage or grab the loop of tubing, and as the roller-head assembly is rotated, the notch pulls the loop of tubing onto the rollers of the roller-head assembly. There have been other structures, such as tapering the roller-heads in order to encourage the loop of tubing to be drawn onto the rollers. While these prior art schemes may be effective in their own way, it would be desirable to have a easily manufactured roller-head assembly that would reliably work with loops of tubing that may be severely misaligned with the roller-head assembly and still be drawn onto the rollers of the roller-head assembly and properly mounted for operation of the peristaltic pump.

DETAILED DESCRIPTION OF THE PREFERRED EMBODIMENT

Figure 1:
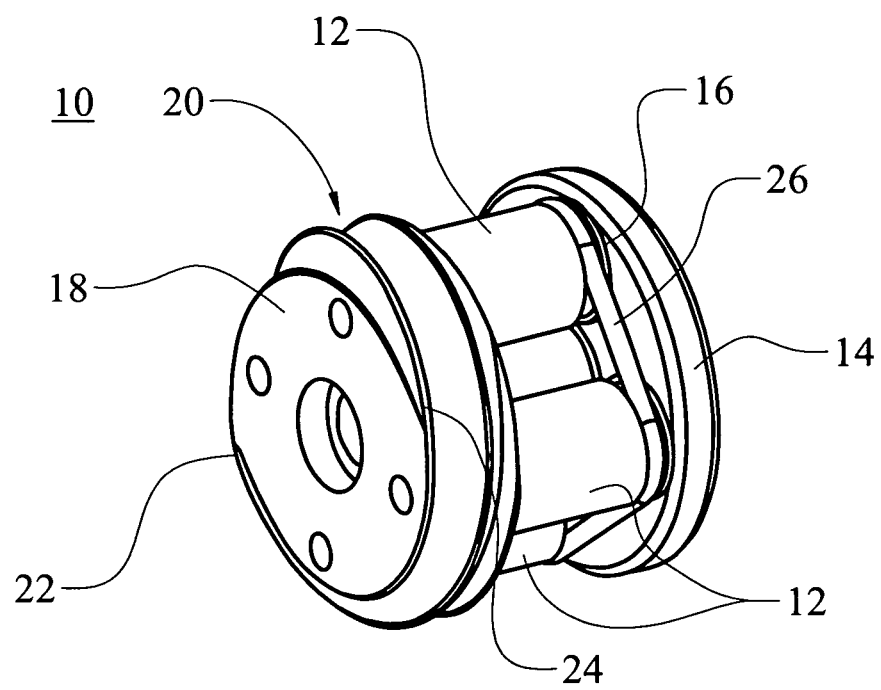
FIG. 1 is a perspective view of a pump roller-head assembly in accordance with the present invention.

FIG. 1 shows an ophthalmic aspiration pump roller-head assembly 10 in accordance with the present invention. Assembly 10 includes a plurality of rollers 12, a base 14 attached to a first end 16 of the rollers 12, and a face-plate 18 attached to a second end of the rollers 12. The face-plate preferably has at least one groove 20 formed about the periphery of the face-plate 18 for drawing a tube onto the rollers 12. More preferably, the face-plate groove 20 includes the shown tapered double-start-screw thread which begins at numerals 22 and 24. It is preferable that groove 20 be formed in face-plate 18 to form at least one complete revolution about the circumference of the face-plate 18, and more preferably, includes a double-start groove, wherein multiple revolutions about the circumference of face-plate 18 are formed. Assembly 10 also preferably includes band 26 which functions to keep the rollers 12 in tight contact with the internal roller shafts to reduce the occurrence of audible noise when the roller-head assembly 10 rotates Roller-head assembly 10 preferably is mounted on a peristaltic pump, such as that described in U.S. Patent Publication 2005/0069419 entitled Peristaltic Pump with Air Venting Via the Movement of a Pump Head or a Backing Plate During Surgery, the contents of which are hereby incorporated by reference and are assigned to the present Assignee. In use, as a cassette drawer closes, the roller-head assembly 10 would be rotated. As the peristaltic tubing engages the roller-head assembly 10, the rotation coupled with the groove 20 serves to draw the tube in over the rollers 12 for proper positioning.

There are several factors that may lead to improper tube loading and positioning. These factors include variations in the tube length, twisting of the tube during manufacture, the tubing being deformed during packaging and shipping, and manufacturing induced curvature of the tubing. If the tubing does not properly load, the result can be a failure of the pump to produce a consistent peristaltic pumping action. In addition, it has been found that if the tubing is only partially loaded on to the rollers 12 particulate due to friction of between rotating pump-head and the tubing can result, which is highly undesirable in a surgical field.

It has been found through empirical testing that severely deformed, twisted, and misaligned tubing loops are easily and properly loaded onto the rollers 12 of the present inventive roller-head assembly 10. While the present invention is depicted incorporating a groove 20, it is believed that other embodiments of a face-plate having asymmetrically placed bumps or other structure may also function to draw the tubing onto rollers 12.

Loading an ophthalmic surgical pump cassette 28 onto aspiration pump roller-head assembly 10 includes the following steps. The roller-head assembly 10 is provided on the pump 30. The roller-head assembly 10 has a plurality of rollers 12, as shown above, attached between the base 14 and face-plate 18.

Figure 3:
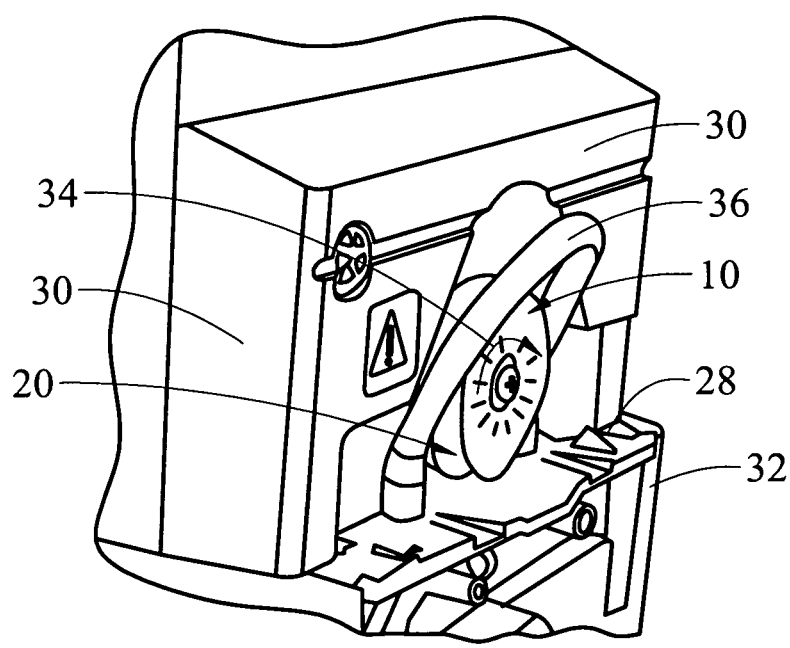
FIG. 3 is the same view as FIG. 2 with the pump drawer partially closed.
Figure 4:
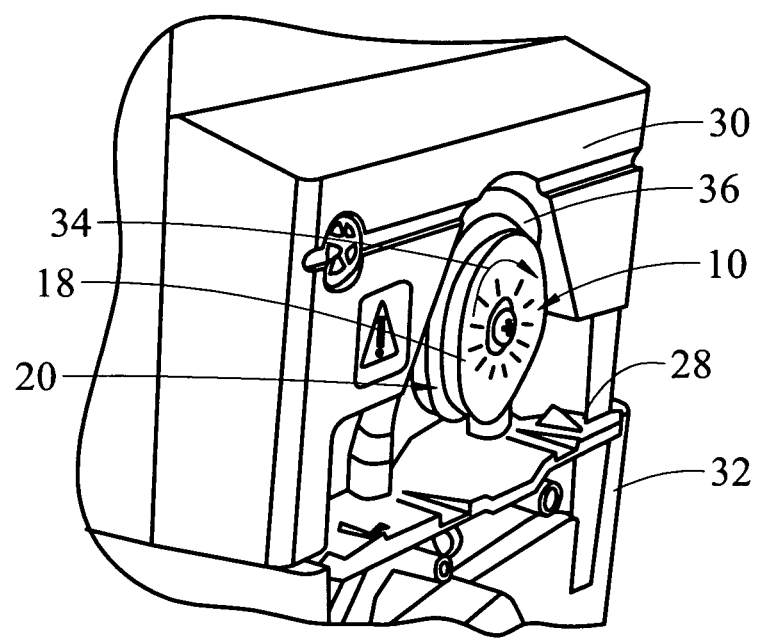
FIG. 4 is the same view as FIG. 2 with the pump drawer fully closed.

Pump 30 preferably provides a drawer 32 for receiving the cassette 28. Cassette 28 may be loaded in the drawer 32 by a user. The pump 30 then causes the drawer 32 to move towards the roller-head assembly 10, as the roller-head assembly is rotated, as indicated by arrow 34. The groove 20 formed in the face-plate 18 causes tube 36 of the cassette 28 to be drawn onto the rollers 12 even when the tube 36 is misaligned with the roller-head assembly 10, as shown in FIGS. 2-4.

Figure 2:
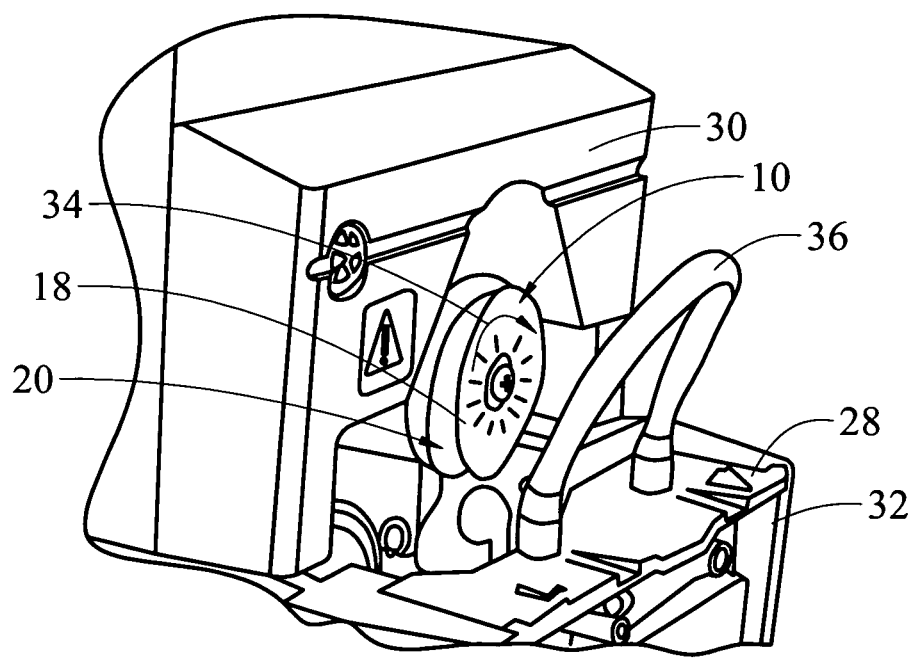
FIG. 2 is a partial perspective view of a pump roller-head assembly in accordance with the present invention installed on a pump with a cassette drawer in a fully opened position.

FIG. 2 shows a peristaltic pump 30 having a cassette 28 loaded into a drawer 32 with a severely misaligned tube loop 36. As the drawer 32 is closed by pump 30, as shown in FIG. 3, the rotation of roller-head assembly 10 causes groove 20 to grab tubing loop 36 and draw the tube 36 onto the rollers 12. FIG. 4 shows the drawer in a closed position with tubing loop 36 properly loaded onto roller-head assembly 10.

Thus, there has been shown an inventive roller-head assembly 10 and method of its use, wherein roller-head assembly 10 is rotating as drawer 32 is closed, the roller-head assembly 10 with groove 20 operates to pull tubing loop 36 onto rollers 12 for proper operation.

What is claimed:

1. An ophthalmic aspiration pump roller-head assembly comprising:
   a plurality of rollers;
   a base attached to a first end of the plurality of rollers;

a face-plate attached to a second end of the plurality of rollers and having at least one groove formed in the face-plate for grabbing a tube and drawing the tube onto the plurality of rollers; and wherein the face-plate groove includes a tapered double-start screw thread.

2. A method of leading an ophthalmic surgical pump cassette onto an aspiration pump roller-head assembly comprising the steps of:

providing a roller-head assembly on the pump, the roller-head assembly having a plurality of rollers attached between a base and a face-plate;

providing a drawer for receiving the cassette;

loading the cassette in the drawer, and causing the pump to move the drawer towards the roller-head assembly as the roller-head assembly is rotated, such that a groove formed in the face-plate causes a tube of the cassette to be drawn onto the plurality of rollers even when the tube is misaligned with the roller-head assembly.

3. The method of claim 2 further comprising the step of forming a tapered double-start screw thread in the face-plate.

* * * * *